United States Patent [19]

Tagnon

[11] Patent Number: 4,554,917

[45] Date of Patent: Nov. 26, 1985

[54] LASER OPHTHALMOLOGICAL SURGICAL DEVICE

[75] Inventor: Luc Tagnon, Saint Mande, France

[73] Assignee: Essilor International Cie Generale d'Optique, Creteil, France

[21] Appl. No.: 480,106

[22] Filed: Mar. 29, 1983

[30] Foreign Application Priority Data

Apr. 1, 1982 [FR] France ................. 82 05654

[51] Int. Cl.⁴ .......................................... A61N 5/02
[52] U.S. Cl. ................................. 128/303.1; 128/395; 351/245
[58] Field of Search ............................. 351/245, 214; 128/303.1, 395, 396, 397, 398; 219/121 EL, 121 EV, 121 EX, 121 LV, 121 LY

[56] References Cited

U.S. PATENT DOCUMENTS

| 3,403,957 | 10/1968 | Wilkinson | 351/245 |
| 3,720,213 | 3/1973 | Hobart et al. | 128/395 |
| 3,891,311 | 6/1975 | Fletcher et al. | 351/245 |
| 4,071,731 | 1/1978 | Baar | 219/121 EL |
| 4,143,660 | 3/1979 | Malyshev et al. | 128/395 |
| 4,165,924 | 8/1979 | Mohrman | 351/245 |
| 4,331,392 | 5/1982 | Sato | 351/214 |
| 4,435,173 | 3/1984 | Siposs et al. | 604/155 |

FOREIGN PATENT DOCUMENTS

| 0007256 | 1/1980 | European Pat. Off. |
| 2344270 | 10/1977 | France |
| WO80/01642 | 8/1980 | PCT Int'l Appl. |

Primary Examiner—Lee S. Cohen
Assistant Examiner—Steven Falk
Attorney, Agent, or Firm—Charles A. Brown; Charles E. Brown

[57] ABSTRACT

An ophthalmological surgical device comprises a laser unit (10) adapted to emit at least one laser beam (F) and an operating unit (11) adapted to focus the laser beam or beams (F) on an aiming point (0). The operating unit (11) incorporates a focusing lens (36) and a mirror (37). These are mounted on a supporting chassis (16) adjustably mounted on a base (24). First control device accessible to the operator control the position of the chassis (16) on the base (24). The lens (36) and mirror (37) are together mounted on an assembly (40) in turn mounted on the support chassis (16). The assembly (40) is movable relative to the chassis (16) under the control of second control device separate from the first control device.

13 Claims, 8 Drawing Figures

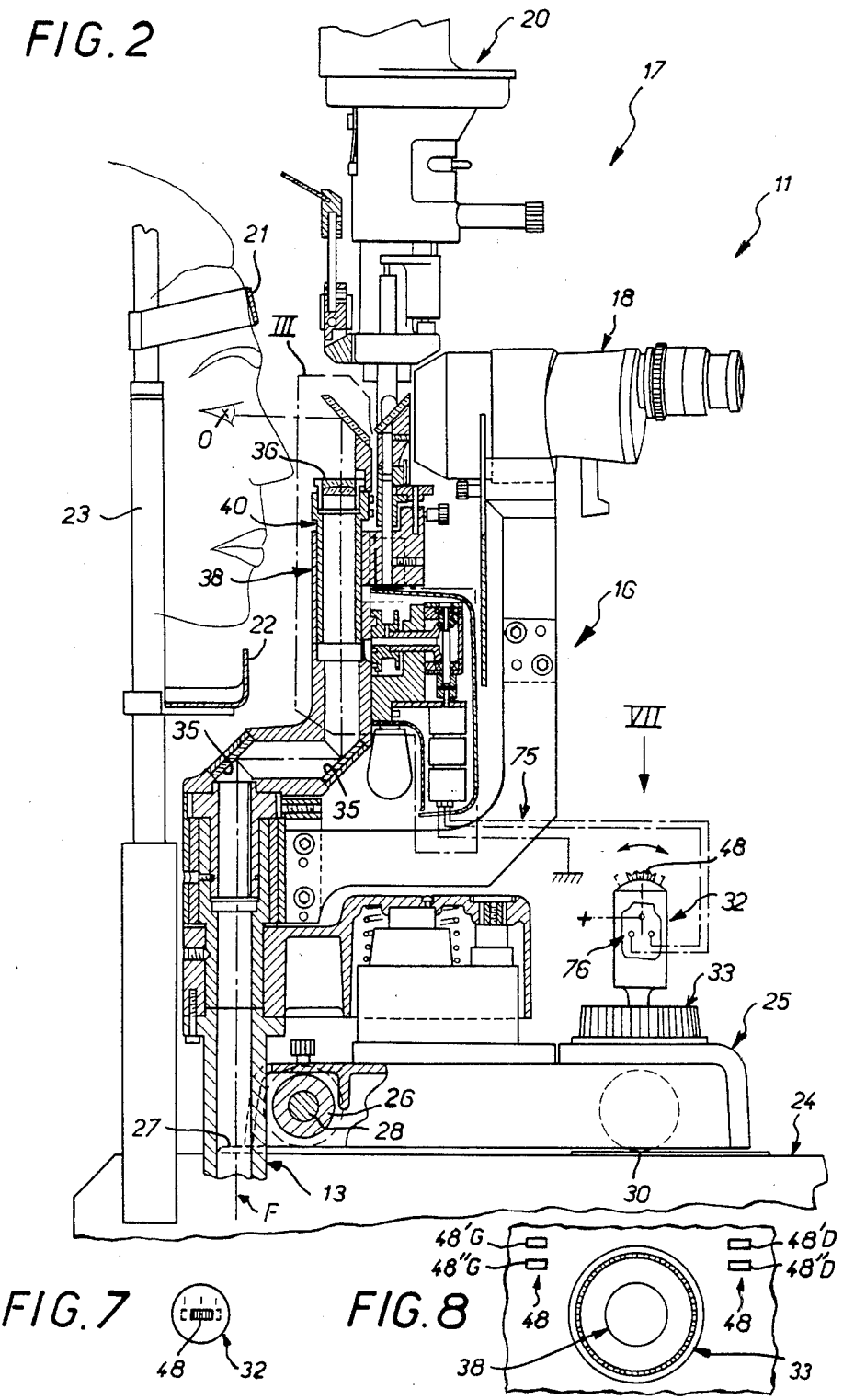

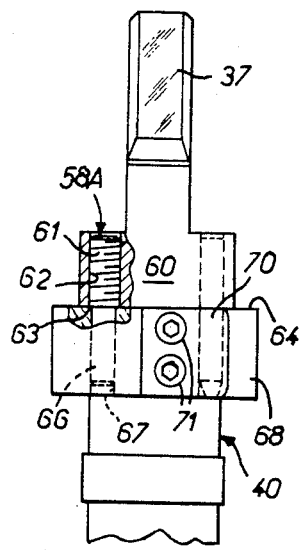
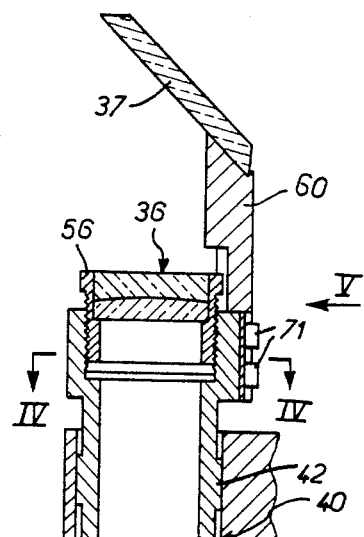
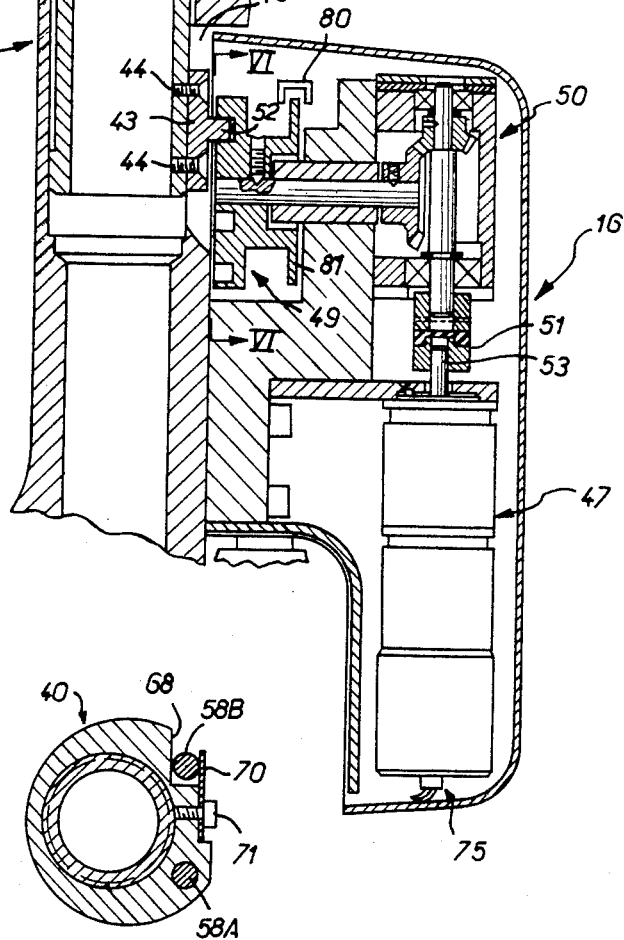
FIG. 5
FIG. 3
FIG. 4
FIG. 6

LASER OPHTHALMOLOGICAL SURGICAL DEVICE

BACKGROUND OF THE INVENTION

1. Field of the Invention

The present invention is generally concerned with laser ophthalmological surgical devices of the type disclosed in European Patent Publication No. 0,007,256 published Jan. 23, 1980 and in U.S. patent application Ser. No. 429,962 filed Sept. 30, 1982 now U.S. Pat. No. 4,517,980, issued May 21, 1985.

2. Description of the Prior Art

Broadly speaking, an ophthalmological surgical device of this kind comprises a laser unit adapted to emit at least one laser beam and an operating unit adapted to focus said laser beam on an aiming point.

In practice, the laser unit preferably comprises two lasers, a main operating laser of sufficiently high power for its beam to operate not by virtue of heat transfer but rather by optical breakdown, a blocked mode YAG laser emitting in the infra-red band being satisfactory for this, and an auxiliary aiming laser producing a visible beam so as to visually indicate the aiming point to the operator, in the form of a red spot of very diameter, for example.

Conjointly, the operating unit usually comprises a slit lamp.

As is known, a slit lamp of this kind generally comprises, on a common support chassis, a microscope adapted to enable the operator to observe the aiming point to be treated, and a slit projector, that is to say a luminous optical device adapted to form a luminous slit in the focusing plane of said microscope, to facilitate observation of the aiming point.

For purposes in particular of adaptation to the morphology of the patient to be treated, the support chassis of a slit lamp of this kind is generally adjustable in position on a base, in practice a plane base, under the control of control means accessible to the operator. The chassis is adjustable parallel to the base, in two orthogonal directions in the plane thereof, one corresponding to a depth adjustment along the aiming axis and the other to a lateral adjustment, perpendicular to the aiming axis. It is also adjustable in height, perpendicularly to said base.

Conventionally, these control means comprise a swinging arm providing depth adjustment when moved forwards and backwards and lateral adjustment when moved to the right and to the left, and also a knob providing the height adjustment, disposed at the base of and around the swinging arm.

It will be apparent that simultaneous manipulation of a swinging arm of this kind and a knob of this kind is difficult.

Also, the operating unit comprises a focusing lens for focusing the laser beam or beams emitted by the laser unit onto the aiming point. For example, and as described in the aforementioned U.S. patent application Ser. No. 429,962, this lens may constitute the exit lens of said laser unit.

In practice, the operating unit further comprises, on the exit side of its focusing lens, a mirror adapted to reflect the laser beam or beams emitted by the laser unit onto the aiming point, the beams being usually incident along the aiming axis whereas the laser unit is disposed to the side of this axis.

Conventionally, this focusing lens and this mirror are fixed in position on the chassis supporting the slit lamp.

An ophthalmological surgical operation normally involves action at a plurality of separate points spaced along a determined path.

To track the aiming point of the laser beam or beams along this path, the operator has previously been required to appropriately and continuously adjust the position of the chassis supporting the slit lamp relative to its base.

As already emphasized, this adjustment of the position of the chassis supporting the slit lamp previously involved the simultaneous manipulation of a swinging arm and a knob, being particularly difficult to achieve in a secure manner in that it requires excellent coordination.

A general object of the present invention is an arrangement intended to facilitate tracking the aiming point along a path.

SUMMARY OF THE INVENTION

The present invention consists in an ophthalmological surgical device comprising a laser unit adapted to emit at least one laser beam and an operating unit adapted to focus said laser beam on an aiming point and including a support chassis, a base on which said chassis is adjustably mounted, first control means for adjusting the position of said chassis on said base, a focusing lens, a mirror on an exit side of said lens, a support assembly on which said lens and said mirror are mounted and which is adjustably mounted on said chassis, and second control means, independent of said first control means, for adjusting the position of said support assembly on said chassis.

In this way the mobile assembly mounting the focusing lens and the mirror has one degree of freedom relative to the supporting chassis, such that its overall displacement is facilitated.

In practice, this mobile assembly is mounted so as to be movable on the supporting chassis along the optical axis of the focusing lens, perpendicular to the base on which the support chassis is mounted, and the second control means associated with it comprise, for this purpose, a motor mounted on the support chassis and an operating member available to the operator controlling the supply of electrical power to the motor.

This operating member is mounted on the swinging arm, for example, of the first control means specific to the supporting chassis.

In an alternative arrangement, it is independent of but accessible from the swinging arm, being disposed in its vicinity.

In either case, the aiming point may be tracked along a path using one hand, controlling the swinging arm for such depth and lateral adjustment as may be necessary and the operating member of the second control means specific to the mobile assembly supporting the focusing lens and the mirror for such height adjustment as may be necessary.

Such simultaneous operation of a swinging arm and an operating member is particularly easy.

When, as described in the aforementioned U.S. patent application Ser. No. 429,962, the focusing lens of the operating unit also constitutes the exit lens of the laser unit, its movement results in defocusing of the laser beam or beams emitted by the laser unit.

However, in view of the length of the optical path on the entry side of the focusing lens, on the one hand, and the relatively limited displacement of the latter for the height adjustment required, on the other hand, such defocusing is virtually undetectable and in practice has no disadvantageous effect.

Other objects and advantages will appear from the following description of an example of the invention, when considered in connection with the accompanying drawings, and the novel features will be particularly pointed out in the appended claims.

BRIEF DESCRIPTION OF THE DRAWINGS

FIG. 2 is a partial cross-sectional view in elevation through the operating unit of the device.

FIG. 3 shows that part of FIG. 2 designated by the box III to a larger scale.

FIG. 4 is a transverse cross-sectional view on the line IV—IV in FIG. 3.

FIGS. 5 and 6 are partially cutaway partial views from the side, in the directions of arrows V and VI in FIG. 3, respectively.

FIG. 7 is a partial view in elevation in the direction of arrow VII in FIG. 2.

FIG. 8 is a view analogous to that of FIG. 7 and relates to an alternative embodiment.

DESCRIPTION OF THE PREFERRED EMBODIMENTS

Figure 1:
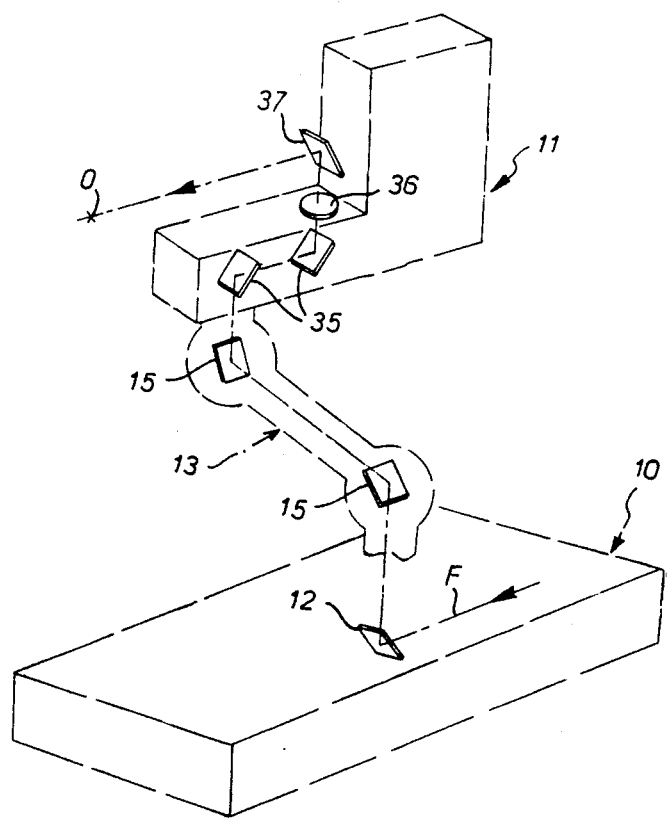
FIG. 1 is a block schematic in perspective of an ophthalmologicalurgical device in accordance with the invention.

As shown schematically in FIG. 1, the ophthalmological surgical device in accordance with the invention generally comprises, in a manner known *per se*, a laser unit 10 adapted to emit at least one laser beam F, represented schematically by a chain-dotted line in FIG. 1, and an operating unit 11 adapted, *inter alia*, to focus said laser beam F on an aiming point O.

As laser unit 10 does not constitute part of the present invention, it will not be described here.

It may be of the kind described in U.S. patent application Ser. No. 429,962 mentioned hereinabove, for example.

The only part of the laser unit represented schematically in FIG. 1 is its exit mirror 12.

In practice, it must be possible to adjust operating unit 11 in position along three mutually perpendicular directions, as will emerge more clearly later, and laser unit 10 is fixed in position. Thus laser unit 10 is linked to operating unit 11 through the intermediary of a transfer arm 13 adapted to permit such relative movement between said units.

Transfer arm 13 does not constitute part of the present invention either, and thus will not be described in detail here.

It may be of the type described in French Patent application No. 81 23947 filed Dec. 22, 1981, for example.

It comprises a plurality of mirrors.

Only the end mirrors 15 are shown schematically in FIG. 1.

Not all details of operating unit 11 will be described here.

Only those parts necessary to an understanding of the invention will be described.

In practice, operating unit 11 comprises, on a supporting chassis of which all component parts are referenced 16, a slit lamp 17 comprising, in a manner known *per se*, a microscope 18 adapted to observe the aiming point O to be treated and a slit projector 20 adapted to form a luminous slit in the focusing plane of microscope 18, in order to facilitate observation of said aiming point O. In practice, this luminous slit is vertical.

Aiming point O is part of the eye of the patient to be treated, the position of which is determined by a forehead support 21 and a chin support 22 mounted so as to be vertically adjustable in position on columns 23 which are in turn rigidly supported on a base 24.

The position of slit lamp 17 must be adjusted to suit the morphology of the patient.

Support chassis 16 carrying this lamp is therefore mounted adjustably on base 24, its position being controlled by control means accessible to the operator.

In practice, and in a manner known *per se*, support chassis 16 is adjustable in height on a baseplate 25 which bears on base 24 at the front via two rollers 26 meshing with respective sprocket rails 27 forming part of base 24 and which are conjointly mounted to slide on a common transverse bar 18 forming part of support chassis 16. At the rear, base plate 25 is supported on base 24 by a ball 30.

As already mentioned, these arrangements are well known *per se* and do not constitute part of the present invention. Thus they will not be described in detail here.

It is sufficient to indicate that the control means associated with support chassis 16 for adjusting its position comprise, for displacement parallel to base 24, a swinging arm 32 which moves backwards and forwards for adjustment in depth along the aiming axis and to the right and left for lateral adjustment perpendicular to this axis. The aforementioned control means further comprise, at the base of swinging arm 32, which in practice consists of a simple lever swingably mounted, a knob 33 which rotates in either direction to adjust the height, by virtue of displacement perpendicular to base 24.

The vertical end of transfer arm 13 is attached to the base of support chassis 16.

In the embodiment shown, in addition to two mirrors 35, operating unit 11 comprises a lens 36 for focusing laser beam F and, on the exit side of the lens, a mirror 37 deflecting laser beam F through 90°.

As described in the aforementioned U.S. patent application Ser. No. 429,962, focusing lens 36 may advantageously also constitute the exit lens of the beam expander(s) usually incorporated in laser unit 10.

Be this as it may, focusing lens 36 and mirror 37 are disposed in the usual manner at the end of a tube 38 constituting an extension of transfer arm 13 within operating unit 11.

Like the end of transfer tube 13, tube 38 is attached to support chassis 16.

In accordance with the invention, focusing lens 36 and mirror 37 are conjointly supported on a supporting assembly 40 which is itself supported by supporting chassis 16, more precisely by the tube 38 attached thereto. It is mounted so as to be movable relative to supporting chassis 16, under the control of second control means separate from the first control means associated with the latter.

In practice, assembly 40 supporting focusing lens 36 and mirror 37 consists of a tube mounted to slide axially within tube 38 (see FIG. 3).

In other words, assembly 40 is slidable within a slideway formed by tube 38.

Thus it is mounted so as to be movable along the optical axis of focusing lens 36, perpendicular to base 24 which mounts support chassis 16.

In practice, the tube constituting assembly 40 incorporates two spaced annular bosses 42 through the intermediary of which it bears on the internal surface of said tube 38 so as to slide therein.

To prevent it rotating in tube 38, it has a longitudinal bar 43 attached to its base, by means of screws 44, for example, which is slidably engaged in a slot 45 formed for this purpose in tube 38.

In the embodiment shown, the second control means associated with assembly 40 comprise a motor 47 mounted on support chassis 16, the supply of electrical power to which is controlled by an operating member 48 accessible to the operator, as will be described in detail hereinafter.

In practice, in the embodiment shown, assembly 40 has a pin 52 projecting from bar 43 by means of which it is engaged with a cam 49 rotatably mounted on support chassis 16 and driven in rotation by output shaft 53 of motor 47 via a right-angle drive 50 and elastic coupling 51.

The necessary constructional details will be apparent to those skilled in the art and thus will not be described in detail here.

As is best seen in FIG. 6, in the embodiment shown cam 49 incorporates a spiral groove 55 in which is engaged pin 52 mounted on assembly 40.

The ends of spiral groove 55 are closed and offset relative to one another in the radial direction, along a common radius in the embodiment shown.

It will be readily understood that, by virtue of the prevention of rotation of assembly 40 on tube 38 mounted on support chassis 16, rotation of cam 49 in respective directions brings about upward and downward axial movement of assembly 40 in tube 38.

In a manner known *per se,* focusing lens 36, which may in practice consist of one, two or more lenses, is supported by a ring 57 screwed to the end of the tube which constitutes assembly 40.

In the embodiment shown, mirror 37 is mounted on assembly 40 through the intermediary of two centering rods 58A, 58B parallel to the axis of focusing lens 36 and therefore to the axis of the tube constituting assembly 40.

Both centering rods 58A, 58B are attached to a block 60 on which mirror 37 is mounted.

Centering rod 58A has a threaded head 61 by means of which it is screwed into a threaded hole 62 in block 60. It has a transverse shoulder 63 which bears on a transverse end face 64 of assembly 40. Beyond shoulder 63 it has a shank 66 by means of which it is slidably engaged in a bore 67 in assembly 40.

Centering rod 58B is maintained in contact with a flat 68 on assembly 40 which constitutes a reference plane, by elastic means consisting, in the embodiment shown, of a simple leaf spring 70 attached to assembly 40 by screws 71.

Thus, as will be readily understood, by rotating centering rod 58A using a screwdriver it is possible to move mirror 37 parallel to the axis of the tube constituting assembly 40, in order to adjust the height of mirror 37 relative to assembly 40.

As it must be able to rotate in either direction, motor 47, which is actually a motor-gearbox unit, is in practice a direct current motor.

The wiring 75 to it is shown schematically in chain-dotted line in FIG. 2.

In outline, and in a manner known *per se,* whereas one of its terminals is permanently connected to ground, a positive voltage may be applied to either of its other terminals.

In the embodiment shown in FIGS. 1 to 7, the supply of power to motor 47 is controlled by a switch 76 itself controlled by operating member 48 provided in accordance with the invention.

In this embodiment, operating member 48 is mounted at the end of swinging arm 32 and consists of a three-position knob.

Switch 76 is accommodated within swinging arm 32.

The necessary construction details, including the connections to be made between operating member 48 and switch 76, will be familiar to those skilled in the art and thus will not be described in detail here.

Be this as it may, with the knob constituting operating member 48 in its center position, shown in full line in FIGS. 2 and 7, the moving contact of switch 76 is itself in a neutral center position.

Motor 47 is not supplied with power and does not operate.

On the other hand, for either extreme position of the knob constituting operating member 48, schematically represented in dashed line in FIGS. 2 and 7, the moving contact of switch 76, which is connected to the corresponding positive supply voltage, is in one of its extreme positions and motor 47 is supplied with power, in one direction for one extreme position and in the other direction for the other extreme position.

Assembly 40 on which focusing lens 36 and mirror 37 are mounted in accordance with the invention is then moved parallel to its axis, upwards or downwards.

Thus to have aiming point O follow a particular trajectory, the operator has only to actuate swinging arm 32 for the depthwise and lateral adjustment necessary and to simultaneously operate the knob constituting operating member 48, using his thumb, in the direction corresponding to any required height adjustment.

Using arrangements known *per se,* this knob may if required be of the kind which automatically returns to its neutral center position as soon as any pressure exerted on it is released.

MODIFICATION

In the alternative embodiment schematically represented in FIG. 8, operating member 48 in accordance with the invention comprises at least one pair of pushbuttons 48', 48" independent of swinging arm 32 but disposed in its vicinity, for example and as shown on baseplate 25 in the immediate proximity of knob 38. Here they are accessible to a finger of the operator while the same hand, as previously, holds and manipulates swinging arm 32, using the thumb and index finger, for example.

In practice, in the embodiment shown, two pairs of pushbuttons are provided, one pair 48'D, 48"D for a righthanded operator, to the right of knob 33, and another pair 48'G, 48"G to the left of the latter, for a lefthanded operator.

These pushbuttons are preferably of the momentary action kind, operative only when pressed. As shown, they are slightly offset towards the front relative to knob 33, and thus relative to swinging arm 32, for easier access from the latter.

When pushbutton 48'D or 48'G is pressed, one terminal of motor 47 is connected to the corresponding positive supply voltage. The other terminal is so connected when pushbutton 48"D or 48"G is pressed.

As previously, motor 47 is thus operated in one direction or the other, and assembly 40 moves upwards or downwards.

In another alternative embodiment, not shown, operating member 48 is a selector knob, a control system provided for this purpose automatically adjusting the position of assembly 40 according to that of the selector knob.

According to a further development of the invention, the supply of electrical power to motor 47 is preferably controlled also by automatic resetting means operative at the end of operation.

For example, and as shown schematically in FIG. 3, three opto-electrical cells 80 (only one of which is shown in the figure) may be disposed for this purpose around a disk 81 which carries a marker for exciting the cells.

The position of one of opto-electrical cells 80 around disk 81 represents the central position of assembly 40, whereas the positions of the other two represent its extreme positions.

Under the control of a special triggering knob, which may, for example, be subject to the control of the unit which normally locks out the footpedal for firing laser unit 10 at the end of operation, a logic system controlled by opto-electrical cells 80 systematically feeds power to motor 47 in one direction.

If, during the resulting rotation of disk 81, the marker on the latter moves past opto-electrical cell 80 whose position represents the central position of assembly 40, the logical system cuts off the supply to motor 47.

If, on the other hand, this marker moves past one of the other two opto-electrical cells 80, the logical system reverses the power supply to motor 47 so as to reverse the direction of movement of assembly 40.

When this arrives at its central position, the cutting off of electrical power supply to motor 47 is brought about by the corresponding opto-electrical cell 80, as previously described.

Various methods of constructing this system will be familiar to those skilled in the art and thus will not be described in detail here.

A knob may be provided for resetting electric motor 47 manually if required, instead of or in addition to the system described above.

It will be understood that various changes in the details, materials and arrangements of parts, which have been herein described and illustrated in order to explain the nature of the invention, may be made by those skilled in the art within the principle and scope of the invention as expressed in the appended claims.

It is claimed:

1. An ophthalmological surgical device comprising a laser means for generating at least one laser beam along a path and an operating means for focusing the one laser beam on an aiming point; said operating means including a base, a support chassis adjustably mounted on said base, first control means for adjusting the position of said chassis on said base, a focusing lens and a mirror on an exit side of said lens arranged along the path of the laser beam when in operation, a support assembly supporting said lens and said mirror and adjustably mounted on said chassis, and second control means, independent of said first control means, for adjusting the position of said support assembly on said support chassis toward and away from said base.

2. A device according to claim 1, wherein said second control means comprise an electric motor mounted on said chassis and an operating means for controlling the supply of electrical power to said motor.

3. A device according to claim 1, wherein said support assembly is adjustably mounted for movement along the optical axis of said lens.

4. A device according to claim 2, wherein said support assembly is slidably mounted in a slideway and has a projecting pin engageable with a cam driven in rotation by said motor.

5. A device according to claim 2, wherein said first control means comprise a swinging arm adapted to move said chassis parallel to said base and carrying said operating means for controlling the supply of electrical power to said motor.

6. A device according to claim 5, wherein said operating means for controlling the supply of electrical power to said motor is a three-position knob disposed at the end of said swinging arm.

7. A device according to claim 2, wherein said first control means comprise a swinging arm adapted to move said chassis parallel to said base and said operating means for controlling the supply of electrical power to said motor is independent of but accessible from said swinging arm.

8. A device according to claim 2, further comprising automatic resetting means operative at the end of operation for resetting the supply of electrical power to said motor and also constituting a further means of controlling the supply of electrical power to said motor.

9. A device according to claim 1, comprising two centering rods parallel to the axis of said lens supporting said mirror on said assembly, one of said rods being slidably engaged in a bore in said assembly, a flat on said assembly and elastic means maintaining the other of said rods against said flat.

10. A device according to claim 9, comprising a block supporting said mirror, a threaded head on said one centering rod, a threaded bore in said block in threaded engagement with said threaded head, and a transverse shoulder on said threaded head bearing on said assembly.

11. A device according to claim 1, wherein said support assembly is adjustably mounted for movement generally perpendicular to said base.

12. A device according to claim 1, wherein said operating means for focusing the one laser beam on an aiming point includes a slit lamp.

13. A device according to claim 3, wherein said support assembly is adjustably mounted for movement perpendicularly to said base.

* * * * *